United States Patent [19]

Weldon

[11] Patent Number: 4,963,306

[45] Date of Patent: Oct. 16, 1990

[54] METHOD FOR MAKING FUSELESS SOFT TIP ANGIOGRAPHIC CATHETER

[75] Inventor: Thomas D. Weldon, Aquadilla, P.R.

[73] Assignee: Novoste Corporation, Aquadilla, P.R.

[21] Appl. No.: 219,583

[22] Filed: Jul. 14, 1988

[51] Int. Cl.$^5$ ................. B29C 53/08; B29C 71/02
[52] U.S. Cl. ....................... 264/101; 264/149;
  264/150; 264/159; 264/209.3; 264/236;
  264/295; 264/339; 264/347; 604/280; 604/264
[58] Field of Search ................. 264/150, 209.6, 149,
  264/236, 159, 101, 345, 346, 339, 347, 295, 296,
  209.7, 209.3, 327; 604/280, 264; 425/403

[56] References Cited

U.S. PATENT DOCUMENTS

| | | | |
|---|---|---|---|
| 3,304,353 | 2/1967 | Harautuneian | 264/296 |
| 3,434,869 | 3/1969 | Davidson . | |
| 3,485,234 | 12/1969 | Stevens . | |
| 3,548,584 | 12/1970 | Silverman et al. | 264/346 |
| 3,606,669 | 9/1971 | Kemble | 264/339 |
| 3,755,525 | 8/1973 | Sheridan et al. | 264/295 |
| 4,211,741 | 7/1980 | Ostoich . | |
| 4,276,250 | 6/1981 | Satchell et al. . | |
| 4,321,226 | 3/1982 | Markling | 264/173 |
| 4,422,999 | 12/1983 | Mitchell | 264/339 |
| 4,551,292 | 11/1985 | Fletcher et al. | 264/173 |
| 4,596,563 | 6/1986 | Pande . | |
| 4,636,346 | 1/1987 | Gold et al. | 264/173 |
| 4,694,838 | 9/1987 | Wijayarthna | 128/658 |
| 4,735,620 | 4/1988 | Ruiz | 604/281 |
| 4,753,765 | 6/1988 | Pande | 264/167 |
| 4,764,324 | 8/1988 | Burnham | 264/173 |

Primary Examiner—Jeffery Thurlow
Attorney, Agent, or Firm—Cook, Egan, McFarron & Manzo

[57] ABSTRACT

Thin-walled catheters are provided which have an elongated fuseless polymeric tube that is made from a single tube of extruded polymer. The elongated fuseless polymeric tube includes a body portion that had been subjected to a high temperature zone in order to solid state polymerize and enhance the mechanical stability, burst strength and kink resistance of the body portion. Also included is a tip portion of the elongated fuseless polymeric tube which was subjected to a low temperature zone to retain the initial properties of extruded polymer.

36 Claims, 2 Drawing Sheets

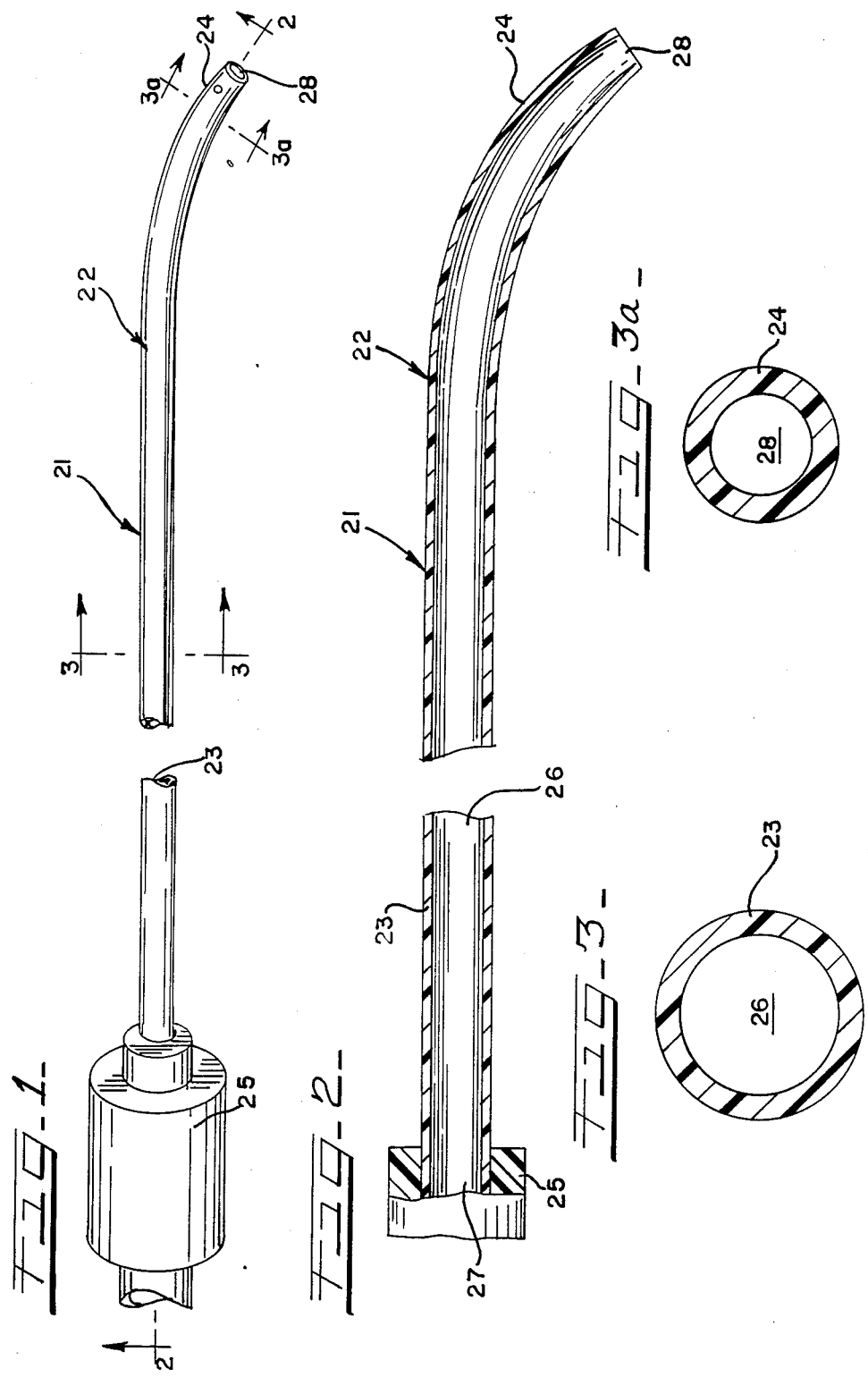

METHOD FOR MAKING FUSELESS SOFT TIP ANGIOGRAPHIC CATHETER

BACKGROUND OF THE INVENTION

The present invention relates to fuseless catheters having a soft tip and to their method of construction. More particularly, this invention relates to the construction of thin-walled angiographic catheters having unique physical properties that are especially advantageous for the efficient passage of relatively large boluses of radiological medium therethrough while exhibiting a soft tip that fuselessly extends from a body having stiffness properties greater than that of the soft tip. The fuseless aspect of the invention includes utilizing solid state polymerization techniques.

Radiological catheters are well known for use in angiographic, diagnostic and therapeutic applications wherein it is necessary to administer a fluid to a location within the cardiovascular system. Because these catheters are used in intravascular systems, they necessarily must have a small outside diameter, as is appreciated in the art. In addition, radiological catheters for angiographic use should be able to deliver large boluses of radiopaque dyes or the like in a relatively short time period. These combined requirements have led the angiographic catheter industry to attempt to provide catheters having an extremely thin-walled construction while still having the ability to introduce contrast material, chemotherapeutic agents, nutritional materials, drugs and other liquid phase medically useful materials into the human bloodstream.

Such thin-walled construction raises concerns regarding meeting strength requirements and burst thresholds. These concerns are especially significant when it is appreciated that these strength and burst requirements typically must be maintained when the angiographic catheter is in contact with radiological fluids and with body fluids which can have a deleterious effect on otherwise suitable catheter shaft materials. Typically, in order to achieve the required high flow rates of radiopaque fluids and the like through small caliber angiographic catheters, such thin-walled catheters must withstand hydrostatic and dynamic pressures on the order of greater than 1,000 psi even when in the presence of radiopaque dyes or the like.

Radiologists typically find it desirable to be able to use a catheter that will permit injection of radiopaque dyes into arteries at a flow rate that is the maximum possible without danger of experiencing catheter rupture. As the outside diameter of the catheter is diminished to allow its entry into smaller vessels, the flow rates tend to be reduced because meeting such an objective typically requires a generally corresponding reduction in the inside diameter of the catheter. Because the fluid must then pass through a narrower cylindrical passageway, extremely high pressures are required in order to maintain high flow rates with small-bore catheters. Consequently, in order to be able to achieve high flow rates, there is an incentive and a tendency to try to minimize the wall thickness of the catheter. This requires a catheter construction which exhibits a high tensile strength when extruded or otherwise formed into a catheter body.

Moreover, this high tensile strength should not be reduced because of the presence of a seam between the body and the tip of the catheter which is generally expensive to fabricate, can cause alignment problems, and could lead to fuse failure during use. Likewise, the tensile strength of such catheters should not be significantly reduced when the catheter is called upon to pass radiopaque dyes, or other substances such as bodily fluids and the like. Any such reduction in tensile strength will restrict the amount of fluid pressure to which the catheter device can be subjected during use, and the radiologist will be limited to the flow rate that is possible without raising a risk of having the catheter burst or develop other possibly dangerous structural defects.

In addition, because catheters such as angiographic catheters typically must be able to reach distant vessels within the body without damaging or tearing the lining of the blood vessels, such catheters must have soft tips and be flexible. Catheter tips are not subjected to high fluid pressures and should preferably be constructed of softer, more flexible material than catheter bodies. Also, after catheter materials are extruded, they must be non-toxic, capable of holding an opaque fluid, non-thrombogenic, smooth-walled, and resistant to kinking. Likewise, catheter materials should be of the type that exhibit a low coefficient of friction.

It is accordingly a general object of the present invention to provide fuseless, soft tip catheters and to a method of making them.

Another object of this invention is to provide catheters that allow exceptionally high flow rates therethrough even when they exhibit an exceptionally small outside diameter.

Another object of this invention is to provide catheters for angiographic use and the like which are made without a circumferential seam or joint.

Another object of the present invention is to provide thin-walled angiographic catheters that exhibit exceptionally improved burst strength while remaining sufficiently flexible so as to permit the catheter to reach distant vessels within the body while minimizing trauma.

Another object of the present invention is to provide thin-walled angiographic catheters that are able to withstand high hoop stress conditions.

Another object of this invention is to provide an improved method and apparatus for making a soft-tipped angiographic catheter that has a fuseless construction which exhibits enhanced burst strength while maintaining a soft tip.

These and other objects, features and advantages of the present invention will be clearly understood through a consideration of the following detailed description.

SUMMARY OF THE INVENTION

It has been found that thin-walled catheters having desirable properties, especially including high tensile strength even when passing radiopaque dyes, can be constructed from extrudable polymers that can be subjected to solid state polymerization such that its physical properties can be altered by exposing the extruded polymer to elevated temperatures. A fuseless or seamless catheter is provided which exhibits a soft-walled tip portion by effecting solid state polymerization of only selected portions of the extruded polymer tube in order to thereby form a catheter which has a stiff, strong body and a pliable, atraumatic tip. The body and the tip are constructed of the same polymer but have differing physical properties. Polyamide materials are especially suitable polymers which undergo solid state polymerization at temperatures between the boiling point of water and the melting point of the polyamide material.

BRIEF DESCRIPTION OF THE DRAWINGS

In the course of this description, reference will be made to the attached drawings, wherein:

FIG. 1 is a perspective view, partially broken away, of an assembled angiographic catheter according to this invention;

FIG. 2 is a longitudinal, cross-sectional view along the line 2—2 of FIG. 1;

FIG. 3 is a transverse cross-sectional view along the line 3—3 of FIG. 1;

FIG. 3a is a transverse cross-sectional view along the line 3a—3a of FIG. 1;

DESCRIPTION OF THE PARTICULAR EMBODIMENTS

Figure 4:
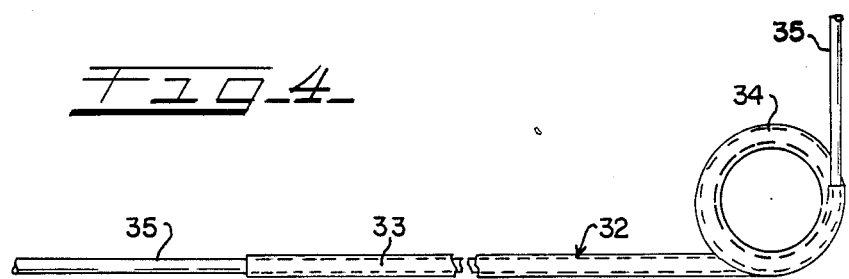
FIG. 4 is an elevational view illustrating a step according to the present invention.

FIG. 1 provides an illustration of the type of catheter, generally designated as 21, which can incorporate the features of the present invention. Catheter 21 includes an elongated fuseless polymeric tube 22 having a body portion 23 and a tip portion 24. A hub member 25 of conventional construction is secured to the elongated fuseless polymeric tube 22. As can be seen in FIGS. 2, 3 and 3a, a longitudinal lumen 26 extends throughout the elongated fuseless polymeric tube 22 from a generally coaxial bore 27 in the hub member 25 to a distal orifice 28 within the tip portion 24.

With more particular reference to the elongated fuseless polymeric tube 22, the body portion 23 and the tip portion 24 are constructed of a unitary sheath or cylinder that was extruded in a single pass out of a precision extrusion device. The body portion 23 is differentiated from the tip portion 24 primarily by virtue of their different physical properties. The tip portion 24 is not in any way assembled onto or secured to the body portion 23 by any type of fusing means such as an adhesive, a solvent bond, a heat sealing procedure, a banding means or the like. If desired, the tip portion 24 can exhibit a gradual tapering of outside diameter which decreases toward the distal orifice 28. It is also typical that catheters of this type will exhibit a degree of curvature which generally includes the tip portion 24. In this regard, FIGS. 1 and 2 show a somewhat gradual curvature, while FIG. 4 illustrates a more complete curvature that is known in the art as a so-called pigtail curl.

With more particular reference to FIG. 4, an elongated fuseless polymer tube 32 includes a body portion 33 and a tip portion 34 which includes the pigtail curl structure. In FIG. 4, the elongated fuseless polymer tube 32 is shown placed onto a stiff wire support mandrel 35, which has a shape which includes that of what will be the body and tip of the finished catheter after same is affixed to a hub member 25 or the like. This support mandrel 35 is useful in imparting the desired shape to the elongated fuseless polymer tube by being shaped to conform with the type of catheter structure that is desired. For example, the support mandrel can be shaped as shown in FIG. 4 so as to impart a pigtail curl to the catheter, or shaped so as to impart the type of tapered curve shown in FIGS. 1 and 2, or shaped to impart a shape typical of or required for angiographic catheters or the like, as will be understood in the art.

Figure 5:
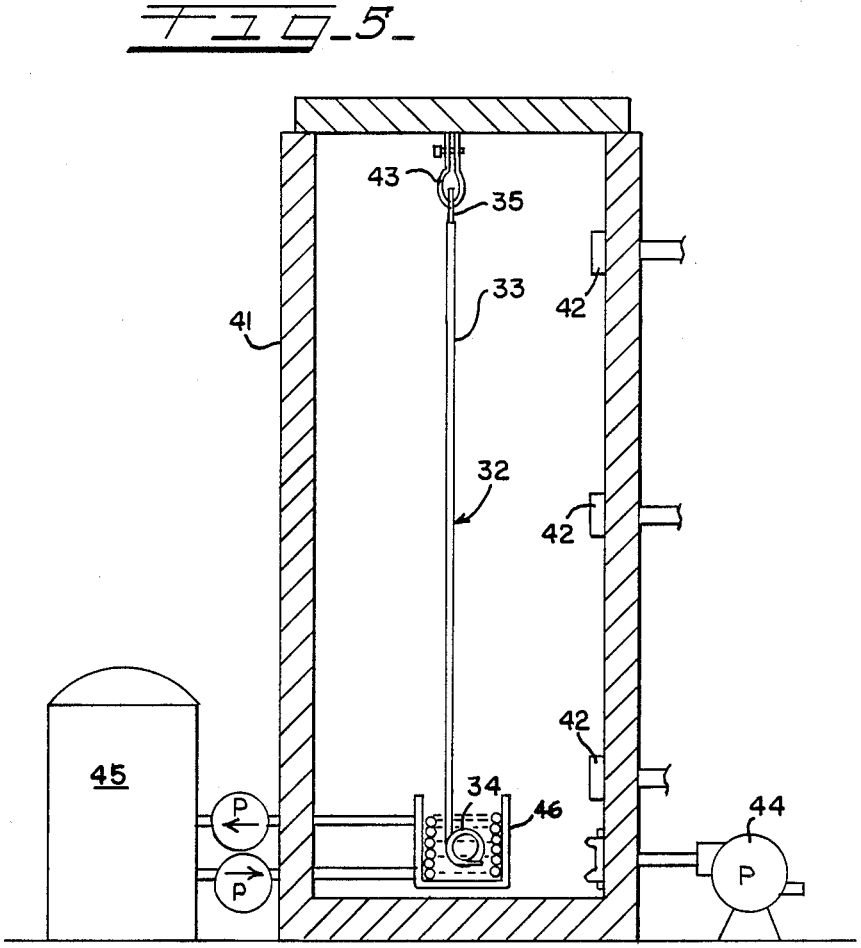
FIG. 5 is a somewhat schematic illustration of a treatment step subsequent to that shown in FIG. 4.

As will be appreciated from a consideration of FIG. 5, the support mandrel 35 also serves to assist in distributing heat more evenly in order to impart the desired physical properties to the body portion 23, 33. With more specific reference to FIG. 5, means are shown for imparting heat energy to the extruded body portion 23, 33 while substantially preventing the application of heat to the tip portion 24, 34 of the elongated fuseless polymer tube 22, 32. The means illustrated in FIG. 5 includes an oven device 41 having one or more heat generators and one or more heat distributors 42. The support mandrel 35 and thus the elongated fuseless polymer sheath are suspended or otherwise positioned within the oven device 41 or the like, such as by means of a hanger assembly 43. With an arrangement such as this, the body portion of the elongated fuseless polymer sheath is subjected to the heat of the oven, such heat distribution being facilitated by wire support mandrel 35. Such heat application effects a solid state polymerization of the extruded polymer throughout the body portion of the elongated fuseless polymer sheath. This procedure can be further facilitated by including an assembly for reducing the pressure, or for drawing a vacuum, within the oven device 41. Such may take the form of a vacuum pump 44 or the like.

Means are further provided in association with the oven device 41 in order to prevent or substantially reduce the application of heat to the tip portion 34 of the elongated fuseless polymer sheath 32. The particular means that are illustrated in this regard in FIG. 5 include a refrigeration unit 45 which chills water or other fluid that is pumped into, circulates within, and is withdrawn from an enclosure 46. This chilled fluid provides a suitable barrier from the heat that is otherwise present within the oven device 41.

After having been treated with an assembly such as that illustrated in FIG. 5, the elongated fuseless polymer tube includes a body portion that has undergone solid state polymerization in order to form same into a less flexible, strong body, while the tip portion which has not been thus subjected to solid state polymerization provides a pliable atraumatic tip portion having soft, flexible properties on the order of those of the extruded and untreated polymer tube. Regarding the solid state polymerization that is carried out by the heat cycle, same is believed to drive off water within the polymer network and to complete polymerization thereof. Application of the vacuum or reduced pressure facilitates evaporation of moisture and decreases the time required to carry out the degree of solid state polymerization that is desired. When, for example, the extruded polymer is a polyamide, the extruded polyamide can include pre-polymeric materials such as amine salts of carboxylic acids. When such salts are heated above their melting points, they are transformed into polyamide groups, with water molecules being liberated. This further, solid state polymerization of the extruded polyamide material increases the strength of the polymer.

The elongated fuseless polymeric tube is made of an extrudable polymer. Extruded polymers include polyamides such as the nylons, as well as polyurethanes, polyolefins, polyacetals such as Delryn, polyvinyls such as polyvinyl chloride, and the like. Typically, the elongated fuseless polymeric sheath will be composed of a single one of these polymers, or it can be made of multiple, coaxial layers of different polymers, for example structures formed by coextrusion. The preferred polymers are polyamides, which are typically condensation polymers prepared by the reaction of a diacid and a diamine having terminal carboxy and diamine groups. Among the polyamide materials useful herein are Nylon 6, Nylon 6/6, Nylon 6/9, Nylon 9, Nylon 11, Nylon 12 and a proprietary nylon, manufactured by Novoste Corporation.

Catheters according to the present invention are manufactured by first extruding one of these polymeric materials onto an air mandrel, a wire mandrel, or other means, typically by utilizing a conventional wire coating extrusion apparatus in order to form a continuous cylindrical extrusion. This continuous extrusion is cut to the length desired for the elongated fuseless polymeric tube, and the forming mandrel, if a solid one is used, is removed. The elongated cut extrusion is then placed on a stiff wire support mandrel or the like. The polymer tube and mandrel assembly is then placed into a heat imparting means as generally described herein, which maintains two distinct temperature zones. The portion of the tube that is to form the body portion of the elongated fuseless polymeric tube is exposed to the high temperature zone, while the portion of the tube that is to form the tip portion of the elongated fuseless polymeric tube is exposed to the low temperature zone. Typically, the high temperature zone will provide a temperature that is greater than the boiling point of water and that is less than the melting point of the polymer. Generally speaking, the low temperature zone will be at a temperature which is less than 80° C., more preferably at room temperature or lower.

After a period of time, typically for at least two hours or more, the support mandrel and elongated fuseless polymeric sheath assembly is removed from the oven. If desired, as is often the case, the curved tip portion is thermoformed by dipping same into boiling water or the like for a short period of time (on the order of a few minutes) and then dipping same in a cooler material (such as ice water) for another short period of time (typically a few minutes). The thus completed elongated fuseless polymeric tube is then removed from the stiff wire support mandrel, and the catheter assembly is completed by finishing the surface and attaching suitable additional members such as a strain relief and a conventional needle fitting to the proximal end of the thus formed catheter device.

Catheters according to the present invention are capable of delivering large boluses of radiopaque dyes in the relatively short time periods that are desired during an angiographic examination or the like. This requires, besides other important attributes of the invention, a body portion that is as thin-walled as possible. The elongated fuseless polymeric tube, should be as thin as possible in order to permit an adequate flow of fluid through the catheter while still permitting passage of the catheter through body vessels. A typical angiographic catheter of the type herein described will be made of a tube so as to form a catheter having a French Size ranging from No. 2 to No. 6.

The solid state polymerization that is carried out according to the present invention will reduce the ability of radiopaque dyes and other fluids which pass through the catheter, and through which the catheter passes, from deteriorating the extrudable polymer. This provides the important result that the elongated fuseless polymeric sheath according to the present invention will retain the tensile strength and burst resistance that it exhibits in air even when the catheter assembly is contacted for extended time periods with body fluids or radiological media, including those which contain iodine or other deleterious materials.

For example, the use of the present invention has provided catheters which provide an increased flow rate of radiopaque fluids, such increases being by at least 20 percent to up to 25 percent or more for polyamide catheters of French Size No. 4. More specifically, when using a French Size No. 4 polyamide catheter that is not subjected to solid state polymerization according to the present invention, it has been difficult to attain a flow rate of on the order of 20 ml per minute. Using an otherwise identical catheter that has been subjected to solid state polymerization according to the present invention, flow rates of at least about 25 ml per minute, including flow rates of about 26 ml per minute, are readily attained.

The solid state polymerized catheter body according to the present invention protects the extruded polymer from deterioration or detrimental change in properties upon contact with radiological fluids, water, blood and other fluids passing through or otherwise contacting the catheter. This attribute is especially important for angiographic catheters and the like. If, due to deterioration by a radiological fluid or the like, portions of a polyamide catheter sheath or body were to break off and remain in a patient's body for extended time periods, polyamides have a tendency, under those conditions, to depolymerize and release monomers which can raise toxicity concerns. Such concerns are substantially eliminated by the present invention. Also, polyamides which are extruded and not solid state polymerized tend to absorb water from contact with blood or tissue, and the absorbed water can lead to plasticizing of the polyamide polymer. When a radiological medium such Renographin 76 (supplied by Squibb) or Hypaque is brought into contact with a polymer that has not been solid state polymerized, it can plasticize or soften the polymer, which results in a reduction of its tensile strength and a reduction of its flexural modulus.

The following examples illustrate catheters according to the present invention, as well as their preferred method of manufacture.

EXAMPLE 1

A proprietary polyamide material, which is manufactured by Novoste Corporation, was extruded through a precision extruder into tubing suitable for use in preparation of an angiographic catheter. The extruded tubing was cut to a desired length and positioned on a stainless steel mandrel having a pigtail curl at the distal end portion thereof. This assembly was then placed into an oven device generally in accordance with FIG. 5 which maintains two different temperature zones. The upper or body portion was maintained at a temperature of 120° C., while the lower portion comprising a three inch tip portion which contains the pigtail shape was maintained at 10° C. in chilled water. After two and one-half hours, the catheter was removed from the oven, and the tip assembly was thermally set by immersing the pigtail section in boiling water for three minutes. The assembly was then chilled in ice water for two minutes, after which the mandrel was removed, and the catheter was fully assembled by adding a hub member and the like.

The catheter thus formed was of French Size No. 4. The static burst pressure was measured at 1,400 psi in water. An otherwise substantially similarly manufactured French Size No. 4 Novolon catheter which was not subjected to the solid state polymerization procedure within the oven device exhibited a static burst pressure of approximately 1,000 psi in water. This represents an approximately 40 percent increase achieved by the present invention.

The tip of the catheter, which was exposed to the low temperature zone, was noticeably more pliable and bends further under load before kinking occurs than does the body portion or shaft of the catheter device made according to this example.

EXAMPLE 2

A catheter is made generally in accordance with Example 1. However, after the extruded Novolon material is cut to the desired length, the distal tip portion thereof is tapered, and holes are punched near the distal tip in order to assist in dispersion of the injecting media when the device is used as an angiographic catheter. Also, the high temperature zone is maintained at approximately 125° C., while the low temperature zone is maintained at room temperature or cooler.

EXAMPLE 3

Nylon 6/9 was extruded into French Size No. 4 catheter tubes having an outer diameter of 0.054 inch, an inner diameter of 0.040 inch and a wall thickness of 0.007 inch and this tube was cut to a length suitable for catheter use. The cut tube is inserted over a stiff wire mandrel having a configuration desired for the finished catheter product. This tube and stiff wire support mandrel are heated to a temperature greater than 100° C. and less than the melting point of the nylon polyamide in order to effect solid state polymerization of the polyamide tube. When the thus treated catheter tube is assembled into a catheter and used to inject Renographin 76, better thromboresistant properties are exhibited when compared with untreated Nylon 6/9 catheters exhibiting the same tube dimensions. They do not soften, and they will retain their in-air burst strength of 1,200 psi, a 20 percent improvement over the burst strength of such untreated catheters that deliver boluses of Renographin 76. In addition, the thus treated catheter tubes will have an ultimate elongation at yield of more than 100 percent and a flexural modulus of between about 100,000 and 400,000 psi. Furthermore, the thus treated catheters meet other criteria required and desired by radiologists in that they are non-toxic, are able to be filled with opaque medium, are non-thrombogenic, and exhibit low kinkability.

EXAMPLE 4

A polyurethane is prepared from 1,4-bisphenol isocyanate, polytetramethylene glycol having a molecular weight of about 1,000, and 1,4-butene diol in a manner that is generally known. The preparation is carried out so that the polyurethane exhibits an isocyanate-to-hydroxyl ratio of 0.98. The resulting polyurethane slab is peletized and extruded into a catheter tube having an inner diameter of 0.045 inch and an outer diameter of 0.075 inch. This catheter, which has a wall thickness greater than that of the catheter of Example 3, will have an ultimate tensile strength at yield (burst strength) of approximately 8,000 psi, an ultimate elongation at yield of more than 100 percent, and a flexural modulus of between about 100,000 and 400,000 psi after heat treatment according to conditions specified relative to this invention. When the thus treated polyurethane tubing is assembled into a catheter, same will have a burst strength for passage of radiographic medium that is 20 percent greater than catheters having tubing of the same sizing made from polyurethane which is not so treated.

EXAMPLE 5

Nylon 6/6 is extruded into catheter tubes with an outer diameter of 0.054 inch, an inner diameter of 0.04 inch, and a wall thickness of 0.007 inch. When this tubing is not treated according to the present invention and is assembled into an angiographic catheter, same will demonstrate a burst strength of 1,300 psi in air, 1,100 psi in water and 900 psi in Renographin 76 radiopaque dye. Tubes treated according to the present invention and assembled into catheters will exhibit a burst strength in radiopaque dye of 1,300 psi, which is substantially the same burst strength in air of catheters made with untreated tubes.

It will be understood that the embodiments of the present invention which have been described are merely illustrative of some of the applications of the principles of the present invention. Numerous modifications may be made by those skilled in the art without departing from the true spirit and scope of the invention.

I claim:

1. The method for making elongated, fuseless, polymeric tubing having a first portion which exhibits kink and burst resistance and a second portion which is more pliable than the first portion, the method comprising:
    extruding an elongated, fuseless, polymeric tube having a lumen therewithin;
    heating a first portion of the elongated polymeric tube to an elevated temperature greater than 100° C. but less than the melting point of the polymeric tube for a sufficient time to effect solid state polymerization of the first portion;
    maintaining a second portion of the elongated polymeric tube at a temperature lower than the first portion during the time said first portion is being heated, so as to inhibit solid state polymerization in the second portion and thus provide a second portion which is more pliable than the first portion.

2. The method according to claim 1 further including the steps of placing the elongated polymeric tube on a support mandrel prior to heating, and subsequently removing the elongated polymeric tube from the support mandrel.

3. The method according to claim 1 wherein said lower temperature of the second portion is sufficiently low to substantially prevent solid state polymerization of the second portion.

4. The method according to claim 1, wherein said lower temperature of the second portion is less than 80° C.

5. The method according to claim 1 wherein said lower temperature of the second portion is room temperature or below.

6. The method according to claim 1 wherein the step of heating the first portion includes subjecting the first portion of the elongated polymeric tube to a temperature zone greater than 100° C. but less than the melting point of the polymeric tube.

7. The method according to claim 6 wherein the second portion of the elongated tube is subjected to a lower temperature zone than said first portion.

8. The method according to claim 1 wherein the step of heating includes subjecting the first portion of the elongated polymeric tube to an elevated temperature zone greater than 100° C. but less than the melting point of the polymeric tube and wherein the elevated temperature zone exhibits a pressure that is substantially lower than atmospheric pressure.

9. The method according to claim 2 wherein the support mandrel is a heat conductor which assists in distributing heat to the first portion of the polymeric tube.

10. The method according to claim 1 wherein the polymeric tube is formed of polyamide material.

11. The method according to claim 1 including the steps of:
   forming the second portion of the elongated polymeric tube into a selected shape;
   heating the second portion to an increased temperature for a sufficient period of time such that the second portion will retain the selected shape when cooled, said increased temperature and period of time being sufficient to cause substantial solid state polymerization of the second portion; and
   cooling the second portion.

12. The method according to claim 11 wherein said increased temperature of the second portion is approximately 100° C. and said period of time is a few minutes.

13. The method according to claim 11 wherein said step of heating the second portion includes dipping the second portion into boiling water.

14. The method for making a catheter having an elongated polymeric tube secured to means for introducing fluid into or for receiving fluid from the elongated polymeric tube, the method comprising;
   forming an elongated, fuseless, polymeric tube having a lumen therein;
   placing the elongated polymeric tube on a support mandrel;
   heating one portion of the elongated polymeric tube to an elevated temperature greater than 100° C. but less than the melting point of the polymeric tube for a sufficient time to effect solid state polymerization of said one portion of the elongated polymeric tube;
   maintaining another portion of the elongated polymeric tube at a temperature lower than said one portion during the time said one portion is being heated so as to inhibit solid state polymerization in said other portion; and
   removing the elongated polymeric tube from the mandrel, whereby an elongated fuseless polymeric catheter may be provided having said one portion which exhibits kink and burst resistance and said other portion which is more pliable than said one portion.

15. The method according to claim 14 wherein the step of forming includes extruding the elongated, fuseless, polymeric tube, said one portion of the tube being a body portion and said other portion of the tube being a tip portion.

16. The method according to claim 14 wherein said lower temperature of the other portion is sufficiently low to prevent substantial solid state polymerization of the other portion.

17. The method according to claim 14 wherein said lower temperature of the other portion is less than 80° C.

18. The method according to claim 14 wherein said lower temperature of the other portion is room temperature or below.

19. The method according to claim 14 wherein the step of heating the one portion includes subjecting the one portion of the elongated polymeric tube to a temperature zone greater than 100° C. but less than the melting point of the polymeric tube.

20. The method according to claim 19 wherein the other portion of the elongated tube is subjected to a lower temperature zone than said one portion.

21. The method according to claim 14 wherein the step of heating includes subjecting the one portion of the elongated polymeric tube to an elevated temperature zone greater than 100° C. but less than the melting point of the polymeric tube and wherein the elevated temperature zone exhibits a pressure that is substantially lower than atmospheric pressure.

22. The method according to claim 14 wherein the support mandrel is a heat conductor which assists in distributing heat to the one portion of the polymeric tube.

23. The method according to claim 14 wherein the polymeric tube is formed of polyamide material.

24. The method according to claim 14 including the steps of:
   forming the other portion into a selected shape;
   heating the other portion to an increased temperature for a sufficient period of time such that the other portion will retain the selected shape when cooled, said increased temperature and period of time being insufficient to cause substantial solid state polymerization of the other portion; and
   cooling the other portion.

25. The method according to claim 24 wherein said increased temperature of the other portion is approximately 100° C. and said period of time is a few minutes.

26. The method according to claim 24 wherein said step of heating the other portion includes dipping the other portion into boiling water.

27. The method for making a catheter having a fuseless, one-piece body and tip portion and being free of separate reinforcement for the body, the catheter when in use being suitable for rapidly introducing pressurized fluids into the human bloodstream, the method comprising:
   precision forming an elongated, fuseless, thin-walled polymeric tube of material comprising polyamide material, the tube having a lumen throughout its length and being of fuseless, one-piece construction, free of separate reinforcement;
   placing the elongated polymeric tube on a support mandrel having a selected shape;
   heating a generally elongated body portion of the polymeric tube to an elevated temperature greater than 100° C. but less than the melting point of the polymeric tube for a sufficient time to effect solid state polymerization of said body portion of the polymeric tube;
   maintaining a tip portion of the elongated polymeric tube at a temperature sufficiently lower than said body portion during the time said body portion is being heated so as to inhibit solid state polymerization of the tip portion and provide a tip portion which is more pliable than the body portion; and
   removing the polymeric tube from the mandrel, whereby a catheter may be provided having a body portion which is kink and burst resistant and a tip portion which is more pliable and atraumatic tip portion.

28. The method according to claim 27 wherein said lower temperature of the tip portion is less than 80° C.

29. The method according to claim 27 wherein said lower temperature of the tip portion is room temperature or below.

30. The method according to claim 27 wherein the step of heating the body portion includes subjecting the body portion of the elongated polymeric tube to a temperature zone greater than 100° C. but less than the melting point of the polymeric tube.

31. The method according to claim 30 wherein the tip portion of the elongated tube is subjected to a lower temperature zone than said body portion.

32. The method according to claim 27 wherein the step of heating includes subjecting the body portion of the elongated polymeric tube to an elevated temperature zone greater than 100° C. but less than the melting point of the polymeric tube and wherein the elevated temperature zone exhibits a pressure that is substantially lower than atmospheric pressure.

33. The method according to claim 27 wherein the mandrel is a heat conductor which assists in distributing heat to the body portion of the polymeric tube.

34. The method according to claim 27 including forming the tip portion into a selected shape;
heating the tip portion to an increased temperature for a sufficient period of time such that the tip portion will retain the selected shape when cooled, said increased temperature and time period being insufficient to cause substantial solid state polymerization in the tip portion;
and cooling the tip portion.

35. The method according to claim 21 wherein said increased temperature of the tip portion is approximately 100° C. and said period of time is a few minutes.

36. The method according to claim 34 wherein said step of heating the tip portion includes dipping the tip portion into boiling water.

* * * * *